United States Patent
Kato et al.

(10) Patent No.: US 7,049,455 B2
(45) Date of Patent: May 23, 2006

(54) PROCESS FOR PRODUCING SHOGAOLS AND INTERMEDIATES FOR THE SYNTHESIS THEREOF

(75) Inventors: Hisatoyo Kato, Tsukuba (JP); Shuhei Yamaguchi, Tsukuba (JP)

(73) Assignee: Toagosei Co., Ltd., Tokyo (JP)

( * ) Notice: Subject to any disclaimer, the term of this patent is extended or adjusted under 35 U.S.C. 154(b) by 13 days.

(21) Appl. No.: 10/514,130

(22) PCT Filed: Apr. 25, 2003

(86) PCT No.: PCT/JP03/05377

§ 371 (c)(1),
(2), (4) Date: Nov. 12, 2004

(87) PCT Pub. No.: WO03/095424

PCT Pub. Date: Nov. 20, 2003

(65) Prior Publication Data

US 2005/0159611 A1   Jul. 21, 2005

(30) Foreign Application Priority Data

May 13, 2002  (JP) ............................. 2002-137721

(51) Int. Cl.
*C07C 303/00* (2006.01)

(52) U.S. Cl. ........................ 558/51; 568/310

(58) Field of Classification Search ............... 558/51; 568/310

See application file for complete search history.

(56) References Cited

OTHER PUBLICATIONS

Matsuda et al., Hepatoprotective, superoxide scavenging, and antioxidative activities of aromatic constituents from the bark of *Betula platyphylla* var. japonica, Bioorganic and Medicinal Chemistry Letters 8 (1998) 2939-2944.*

\* cited by examiner

*Primary Examiner*—Johann Richter
*Assistant Examiner*—Chukwuma Nwaonicha
(74) *Attorney, Agent, or Firm*—Sughrue Mion, PLLC

(57) ABSTRACT

In accordance with the invention, an industrial process for producing shogaols useful in the fields of for example foods, flavor, pharmaceutical products, qui-pharmaceutical products and cosmetics can be provided. The invention relates to novel intermediates represented by the following general formula and a process for producing shogaols from the intermediates. In accordance with the invention, shogaols can readily be produced, of which mass production has been difficult because shogaols have been produced only by the extraction process from a natural ginger.

Intermediates;

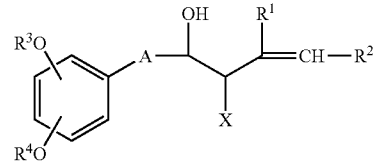

(in the formula (1), $R^1$ represents hydrogen atom or methyl group; $R^2$ represents optionally branched alkyl group with one to 18 carbon atoms; $R^3$ and $R^4$ each independently represents hydrogen atom, a lower alkyl group or a protective group of the phenolic hydroxyl group; A represents an alkylene group with one to 4 carbon atoms; and X represents benzenesulfonyl group or toluenesulfonyl group.)

19 Claims, No Drawings

PROCESS FOR PRODUCING SHOGAOLS AND INTERMEDIATES FOR THE SYNTHESIS THEREOF

TECHNICAL FIELD

The present invention relates to a process for producing shogaol as a hot component contained in ginger and compounds with chemical structures and properties close to those of shogaol (these are collectively referred to as shogaols hereinafter), as well as intermediates for use in synthetically preparing the compounds. Shogaols as subjects of the invention are useful in the fields of foods, pharmaceutical products, qui-pharmaceutical products, cosmetics and the like.

BACKGROUND ART

Shogaols have been known to have antipyretic action, analgesic action, anti-inflammatory action, antioxidant action and an action to suppress biosynthesis of prostaglandin in addition that shogaols are used as food flavor. Shogaols are very important compounds industrially (for example, "Development of Pharmaceutical Products", Vol. 2, Pharmacologically Active Substances II, 1988 edition, Hirokawa Shoten). However, shogaols exist only at a trace amount in naturally occurring materials. Additionally, the isolation and purification of shogaols from naturally occurring materials requires laborious works. Thus, the development of an industrial method for producing shogaols via chemical reactions has been desired.

As a process for producing shogaols, a method is known, which includes a step of reacting gingeron and an aliphatic aldehyde together in the presence of a base to prepare gingerols and further heating the resulting gingerols in the presence of an acid catalyst for dehydration to modify the gingerols into shogaols (Official Gazette of JP-A-8-40970). However, the method described in the Official Gazette was problematic in that the yield of gingerols was so low despite the use of an excess amount of the aliphatic aldehyde that shogaols could not be obtained at a good yield.

It is an object of the invention to provide a process for producing shogaols, by which shogaols can be produced at a high yield.

DISCLOSURE OF THE INVENTION

The present inventors made investigations so as to overcome the problem. Consequently, the inventors found intermediates from which shogaols could be recovered at a high yield. Thus, the invention has been achieved.

In other words, the invention relates to a process for producing a compound represented by the following general formula (1) and additionally to a process for producing shogaols represented by the following general formula (2) from a compound represented by the general formula (1) as a raw material. In accordance with the invention, further, compounds where the phenolic hydroxyl group in shogaols is protected with a protective group are also referred to as shogaols.

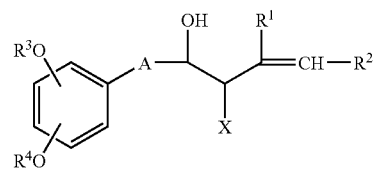

In the formula (1), $R^1$ represents hydrogen atom or methyl group; $R^2$ represents an alkyl group with one to 18 carbon atoms; $R^3$ and $R^4$ each independently represents hydrogen atom, a lower alkyl group or a protective group of the phenolic hydroxyl group; A represents an alkylene group with one to 4 carbon atoms; and X represents benzenesulfonyl group or toluenesulfonyl group.

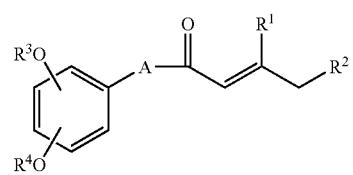

In the formula (2), $R^1$ represents hydrogen atom or methyl group; $R^2$ represents an alkyl group with one to 18 carbon atoms; $R^3$ and $R^4$ each independently represents hydrogen atom, a lower alkyl group or a protective group of the phenolic hydroxyl group; and A represents an alkylene group with one to 4 carbon atoms.

The invention is now described in more detail hereinbelow. A first aspect of the invention is a compound represented by the general formula (1) [referred to as compound of the formula (1); compounds represented by other general formulas are also abbreviated as described above] and are intermediates for shogaols as subjects to be produced in a second aspect of the invention.

The compound of the formula (1) in accordance with the invention can be synthetically prepared by reacting a compound represented by the following general formula (3), namely the compound of the formula (3) with a compound of the following formula (4) in the presence of a strongly basic compound. Specifically, a strongly basic compound attacks the compound of the formula (3) to withdraw hydrogen atom from the carbon to which a substituent —X is bound, to thereby generate a carbon anion based on the compound of the formula (3). When a compound of the formula (4) is subsequently added to the reaction system, the carbon anion reacts with the aldehyde group in the compound of the formula (4), to synthetically prepare the compound of the formula (1).

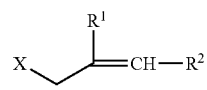

In the formula (3), $R^1$ represents hydrogen atom or methyl group; $R^2$ represents an alkyl group with one to 18 carbon atoms, which may or may not have branched chains; and X represents benzenesulfonyl group or toluenesulfonyl group.

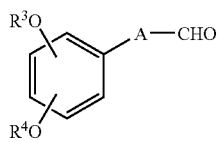

(4)

In the formula (4), $R^3$ and $R^4$ each independently represents hydrogen atom, a lower alkyl group or a protective group for the phenolic hydroxyl group; and A represents an alkylene group with one to 4 carbon atoms.

The compound of the formula (3) can be produced with reference to references such as a reference by K. Inomata, et al., Chem. Lett., 931 (1985).

In the formula (3), $R^2$ represents an alkyl group with one to 18 carbon atoms, which may or may not have branched chains, for example methyl group, ethyl group, propyl group, butyl group, isobutyl group, pentyl group, hexyl group, peptyl group, octyl group, 2-ethylhexyl group, nonyl group, decyl group, lauryl group, and stearyl group. Preferably, the alkyl group is a linear alkyl group with one to 18 carbon atoms. Taking account of the structure of shogaols existing in the natural kingdom, preferably, $R^2$ has carbon atoms of an even number and specifically includes ethyl group, butyl group, hexyl group, octyl group and decyl group.

The compound of the formula (4) can be produced with reference to references such as a reference by G. Solladie, et al., J. Org. Chem., 58, 2181 (1993).

In the formula (4), $R^3$ and $R^4$ each independently represents hydrogen atom, a lower alkyl group or a protective group of the phenolic hydroxyl group. $R^3$ and $R^4$ may be the same or different. The lower alkyl group as $R^3$ and $R^4$ in the formula (4) has preferably one to 3 carbon atoms and is more preferably methyl group. The protective group of the phenolic hydroxyl group in the formula (4) includes for example acetyl group, propionyl group, butyroyl group, isobutyroyl group, pivaloyl group, benzoyl group, toluoyl group, benzyl group, allyl group, trimethylsilyl group and t-butyldimethylsilyl group. Taking account of simple introduction of a protective group into the phenolic hydroxyl group and simple deprotective reaction thereof as well as raw material cost, preferable are acetyl group, propionyl group, butyroyl group, isobutyroyl group, pivaloyl group, benzoyl group, and toluoyl group. Among them, isobutyroyl group and benzoyl group are preferable.

In the formula (4), A represents an alkylene group with one to 4 carbon atoms and is preferably ethylene group or butylene group and more preferably ethylene group.

The strongly basic compound is preferably an alkyl metal compound. Specific examples thereof are alkyl lithium compounds such as n-butyllithium, s-butyllithium, t-butyllithium, and phenyllithium; and Grignard compounds such as n-butylmagnesium chloride, s-butylmagnesium chloride, t-butylmagnesium chloride, n-butylmagnesium bromide, s-butylmagnesium bromide, and t-butylmagnesium bromide. Instead of alkyl metal compounds, alkali metals such as metal lithium and metal sodium may be used as well. Particularly preferable alkyl metal compounds are n-butyllithium, n-butylmagnesium chloride and n-butylmagnesium bromide.

The amount of such strongly basic compound to be used is fundamentally 0.7 to 1.3 chemical equivalents, preferably 0.9 to 1.1 chemical equivalents to that of the compound of the formula (3).

The reaction of the compound represented by the formula (3) with such strongly basic compound is preferably carried out in a non-polar solvent. As such solvent, preferably, tetrahydrofuran, 1,4-dioxane, diethyl ether, 1,2-dimethoxyethane, hexamethylphosphoric triamide, N,N-dimethylpropylene urea and mixture solvents thereof can be used.

The reaction temperature between the compound of the formula (3) and such strongly basic compound is preferably $-100°$ C. to $25°$ C., more preferably $-80°$ C. to $0°$ C. When the reaction temperature is too low, the temperature is retained at high cost, while side reactions may sometimes proceed when the reaction temperature is too high.

The reaction time varies depending on the conditions, but is generally several minutes to several tens of minutes.

Continuously, the compound of the formula (4) is added to the reaction solution to react the carbon anion with the aldehyde group. The temperature of the reaction system then is preferably $-100°$ C. to $25°$ C., preferably $-80°$ C. to $0°$ C. When the reaction temperature is too low, the temperature is retained at high cost, while side reactions may sometimes proceed when the reaction temperature is too high. The reaction time varies depending on the conditions but is generally several minutes to several tens of minutes.

After completion of the reaction, the compound of the formula (1) can be isolated and purified by known processes such as solvent extraction and column chromatography.

The second aspect of the invention, namely the process for producing shogaols from the compound of the formula (1) as the raw material is now described below.

In accordance with the second aspect of the invention, shogaols represented by the general formula (2) (referred to as shogaols of the invention hereinbelow) are produced from the compound of the formula (1) as the starting material. Specifically, the ethylenic unsaturated bond in the compound of the formula (1) reacts with a metal catalyst for forming π-allyl complex; then, the resulting π-allyl complex reacts with a basic compound, to synthetically prepare the shogaols of the invention. In the π-allyl complex formed from the compound of the formula (1) and such metal catalyst, the hydrogen atom bound to the carbon to which hydroxyl group is bound is activated, so that the hydrogen atom is readily withdrawn with the basic compound concurrently existing in the reaction system. Consequently, the π-allyl complex is decomposed to generate the shogaols of the invention.

The metal catalyst for forming such π-allyl complex via reaction with the compound of the formula (1) preferably includes palladium complex compounds, and specifically includes for example tetrakis-triphenylphosphine palladium (valence zero), tris(dibenzylideneacetone) dipalladium (valence zero), chloroform adducts, palladium chloride (divalence)/triphenylphosphine mixture, palladium acetate (divalence)/triphenylphosphine mixture, and palladium acetate (divalence)/tributylphosphine mixture. The description in parentheses means the number of the valence of metal palladium in each of the compounds.

The amount of such metal catalyst to be used is preferably 0.0001 to 1 mol, more preferably 0.0001 to 0.1 mol, particularly preferably 0.0005 to 0.05 mol per one mol of the compound of the formula (1).

When the amount of such metal catalyst used is too less, the progress of the reaction is so slow. When the amount thereof is too much, laborious works are needed to remove such catalyst.

The basic compound for use in the reaction is preferably tertiary amines such as triethylamine, diisopropylethylamine, N-methylimidazole, and pyridine. The amount thereof to be used is 0.9 mol or more per one mole of the compound of the formula (1), and is preferably within a range of 1.0 mol to 10 mol per one mole of the compound of the formula (1). Such basic compound may satisfactorily be used as a solvent.

The reaction is preferably carried out in the presence of a solvent. As such solvent, tetrahydrofuran, 1,4-dioxane, diethyl ether, 1,2-dimethoxyethane, acetonitrile, chloroform, dichloromethane, 1,2-dichloroethane, hexamethylphosphoric triamide, N,N-dimethylpropylene urea, methanol, ethanol, isopropyl alcohol, ethylene glycol, glycerin and mixture solvents thereof can be used. Among them, a mixture of three solvents, namely 1,2-dichloroethane, isopropyl alcohol and glycerin is preferable.

The reaction temperature is within a range of ambient temperature to 150° C., preferably a range of 50° C. to 120° C. The reaction time varies depending on the conditions, but is generally several hours to several tens of hours.

After completion of the reaction, the shogaols of the invention can be obtained by known methods such as solvent extraction and column chromatography. When $R^3$ and $R^4$ in the general formula (2) are protective groups of the phenolic hydroxyl group, the protective groups can be eliminated by general methods.

It was found that [6]-shogaol as one type of shogaol naturally existing, namely shogaol with a structure with hydrogen atoms as $R^1$ and $R^3$, butyl group as $R^2$, methyl group as $R^4$, and ethylene group as A, as synthetically prepared according to the method of the invention, inhibited tyrosinase activity. It was further anticipated that the shogaol had a property to inhibit melanin synthesis.

The shogaols of the invention are used as flavor for use in foods and are additionally useful as a flavor component to be added to cosmetics and toiletry products. Further, the shogaols when mixed with excipients and the like can be used as pharmaceutical agents such as external skin agent, antipyretic agent, analgesic agent, anti-inflammatory agent, antitussive agent or antioxidant.

BEST MODE FOR CARRYING OUT THE INVENTION

The invention is now specifically described in the following Examples and Comparative Examples. In the individual formulas shown below, Ts is p-toluenesulfonyl group.

EXAMPLE 1

The intermediate compound M1 (of the following formula (7)) of the invention was synthetically prepared by reacting the compound of the following formula (5) with the compound of the following formula (6).

Compound of the Formula (5);

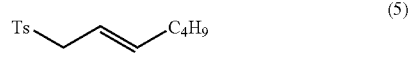

Compound of the Formula (6);

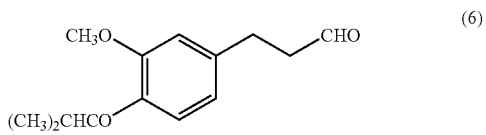

Compound M1;

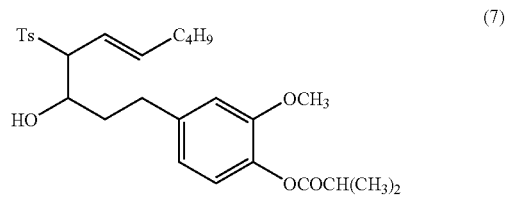

1.81 g (7.17 mmol) of the compound of the formula (5) was dissolved in 30 ml of tetrahydrofuran, and the resulting solution was cooled to −78° C. with dry ice/acetone. To the resulting solution was dropwise added 4.50 ml (7.16 mmol) of 1.59 M n-butyllithium/n-hexane solution. After the resulting mixture was agitated at the same temperature for 20 minutes, a solution of 1.71 g (6.71 mmol) of the compound 2 dissolved in 20 ml of tetrahydrofuran was dropwise added to the mixture. After dropwise addition, the resulting mixture was agitated at the same temperature for 10 minutes. Then, the temperature was gradually elevated. When the temperature of the reaction solution reached −20° C., 2 ml of methanol was added to terminate the reaction.

After 30 ml of saturated aqueous sodium chloride was added to the reaction mixture, extraction in 30 ml of ethyl acetate was done. The extracted aqueous layer was further extracted in 30 ml of ethyl acetate. These ethyl acetate layers were combined together and dried over anhydrous magnesium sulfate. After ethyl acetate was distilled off, purification by silica gel column chromatography was done to obtain a highly viscous, liquid compound of 2.56 g in pale yellow (yield of 75%).

The chemical shift values of the product on $^1$H-NMR spectrum as measured in chloroform-d1 were as follows: 0.73–0.89(3H, m), 0.97–1.37(10H, m), 1.50–2.06(4H, m), 2.44(3H, s), 2.54–3.00(3H, m), 3.15–3.62(1H, m), 3.77(3H, s), 3.94–4.63(2H, m), 5.00–5.85(2H, m), 6.66–6.80(2H, m), 6.85–6.95(1H, m), 7.27–7.37(2H, m), 7.64–7.77(2H, m).

Additionally, the wave numbers (cm$^{-1}$) with absorption by IR absorption spectrometry (KBr pellet method) were as follows: 3510, 2960, 2930, 2870, 1760, 1600, 1510, 1470, 1280, 1180, 1120, 1090, 1030.

Further, the results of elemental analysis were as follows: 67.16% of carbon and 7.38% of hydrogen.

Based on the analysis, it was verified that the obtained compound was the compound M1.

EXAMPLE 2

Using the compound of the formula (5) and the compound of the formula (8), the intermediate compound M2 (of the following formula (9)) was synthetically prepared.

Compound of the Formula (8);

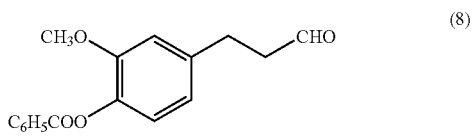

Compound M2;

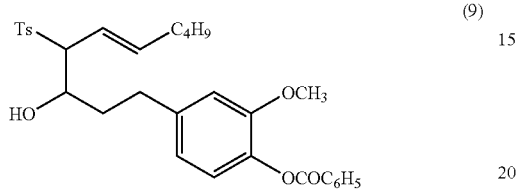

Compound of the Formula (10);

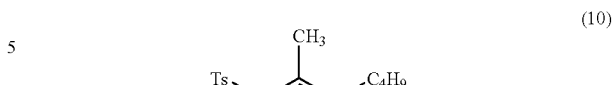

Compound M3;

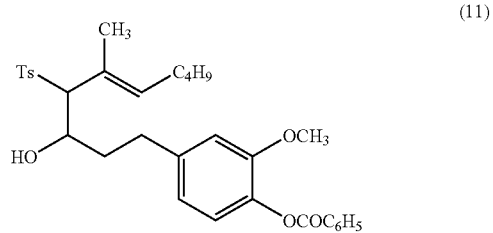

3.46 g (13.7 mmol) of the compound of the formula (5) was dissolved in 50 ml of tetrahydrofuran, and the resulting solution was cooled to −78° C. with dry ice/acetone. To the resulting solution was dropwise added 9.10 ml (13.7 mmol) of 1.50 M n-butyllithium/n-hexane solution. After the resulting mixture was agitated at the same temperature for 20 minutes, a solution of 3.49 g (13.0 mmol) of the compound (8) dissolved in 50 ml of tetrahydrofuran was dropwise added to the mixture. After dropwise addition, the resulting mixture was agitated at the same temperature for 10 minutes. Then, the temperature was gradually elevated. When the temperature of the reaction solution reached −10° C., 2 ml of methanol was added to terminate the reaction. After 30 ml of saturated aqueous sodium chloride was added to the reaction mixture, the mixture was agitated, to separate the organic layer. The aqueous layer was extracted in 30 ml of ethyl acetate. The resulting organic layers were combined together and dried over anhydrous magnesium sulfate. After the solvent was distilled off, purification by silica gel column chromatography was done to obtain a highly viscous, liquid compound of 5.79 g in pale yellow (yield of 79%).

The chemical shift values of the product on $^1$H-NMR spectrum as measured in chloroform-d1 were as follows: 0.72–0.89(3H, m), 0.98–1.24(4H, m), 1.52–2.04(4H, m), 2.45(3H, s), 2.82–2.94(2H, m), 3.16–3.64(1H, m), 3.79(3H, s), 4.04–4.65(2H, m), 5.03–5.85(2H, m), 6.70–6.84(2H, m), 6.96–7.05(1H, m), 7.32(2H, d), 7.45–7.75(5H, m), 8.20(2H, d).

Additionally, the wave numbers (cm$^{-1}$) with absorption by IR absorption spectrometry (KBr pellet method) were as follows: 3520, 2950, 2930, 2870, 1740, 1600, 1510, 1450, 1280, 1260, 1200, 1140, 1120, 1080, 1060, 1020, 710.

Further, the results of elemental analysis were as follows: 69.22% of carbon and 6.55% of hydrogen.

Based on the analysis, it was verified that the obtained compound was the compound M2.

EXAMPLE 3

Using the compound of the formula (10) and the compound of the formula (8), the intermediate compound M3 (of the following formula (11)) was synthetically prepared.

3.65 g (13.7 mmol) of the compound of the formula (10) was dissolved in 50 ml of tetrahydrofuran, and the resulting solution was cooled to −78° C. with dry ice/acetone. To the resulting solution was dropwise added 9.10 ml (13.7 mmol) of 1.50 M n-butyllithium/n-hexane solution. After the resulting mixture was agitated at the same temperature for 20 minutes, a solution of 3.49 g (13.0 mmol) of the compound (8) dissolved in 50 ml of tetrahydrofuran was dropwise added to the mixture. After dropwise addition, the resulting mixture was agitated at the same temperature for 10 minutes. Then, the temperature was gradually elevated. When the temperature of the reaction solution reached −10° C., 2 ml of methanol was added to terminate the reaction. After 30 ml of saturated aqueous sodium chloride was added to the reaction mixture, the mixture was agitated, to separate the organic layer. The aqueous layer was extracted in 30 ml of ethyl acetate. The resulting organic layers were combined together and dried over anhydrous magnesium sulfate. After the solvent was distilled off, purification by silica gel column chromatography was done to obtain a highly viscous, liquid compound of 6.13 g in pale yellow (yield of 81%).

The chemical shift values of the product on $^1$H-NMR spectrum as measured in chloroform-d1 were as follows: 0.71–0.88(3H, m), 0.93–1.21(4H, m), 1.54–2.00(7H, m), 2.44(3H, s), 2.60–3.03(2H, m), 3.22–3.64(1H, m), 3.77(3H, s), 3.92–4.69(2H, m), 4.95–5.54(1H, m), 6.70–6.84(2H, m), 6.96–7.05(1H, m), 7.32(2H, d), 7.45–7.75(5H, m), 8.20(2H, d).

Additionally, the wave numbers (cm$^{-1}$) with absorption by IR absorption spectrometry (KBr pellet method) were as follows: 3510, 2950, 2930, 2870, 1740, 1600, 1510, 1450, 1280, 1260, 1200, 1140, 1120, 1060, 1020, 710.

Further, the results of elemental analysis were as follows: 69.97% of carbon and 7.20% of hydrogen.

Based on the analysis, it was verified that the obtained compound was the compound M3.

EXAMPLE 4

Using the compound M2 obtained in Example 2 as a raw material, the compound S (belonging to shogaols) represented by the following chemical formula (12) was synthetically prepared.

Compound S;

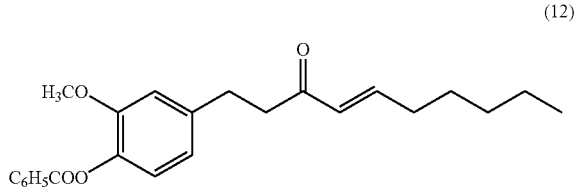

(12)

1.31 g (2.51 mmol) of the compound M2 was dissolved in a mixture solvent of 39 g of 1,2-dichloroethane, 13 g of isopropyl alcohol and 13 g of glycerin. To the resulting solution were added 1.05 ml (7.53 mmol) of triethylamine, 39.5 mg (0.151 mmol) of triphenylphosphine, and 87.0 mg (0.0753 mmol) of tetrakistriphenylphosphine palladium. The resulting mixture was agitated at a bath temperature of 100° C. for 18 hours. After the solvent and the like were distilled off, then, 50 ml of distilled water, 20 ml of aqueous saturated sodium chloride and 50 ml of ethyl acetate were added to the resulting product for partition. The resulting organic layer was separated and isolated. The aqueous layer after extraction was again extracted in 20 ml of ethyl acetate. The combined organic layer was dried over anhydrous magnesium sulfate and then concentrated. The resulting reaction mixture was purified by silica gel column chromatography, and recrystallized in a mixture solvent of ethyl acetate and n-hexane, to obtain a colorless crystallizable compound of 603 mg (yield of 63%).

The chemical shift values of the product on $^1$H-NMR spectrum as measured in chloroform-d1 were as follows: 0.91(3H, t), 1.25–1.60(6H, m), 2.21(2H, q), 2.85–3.00(4H, m), 3.82(3H, s), 6.16(1H, d), 6.79–6.94(3H, m), 7.05(1H, d), 7.45–7.68(3H, m), 8.20(2H, d).

Additionally, the wave numbers ($cm^{-1}$) with absorption by IR absorption spectrometry (KBr pellet method) were as follows: 2950, 2930, 2870, 1730, 1660, 1600, 1510, 1470, 1450, 1420, 1270, 1200, 1150, 1060, 710.

Further, the results of CHN elemental analysis were as follows: 75.56% of carbon and 7.70% of hydrogen.

Based on the analysis, it was verified that the obtained compound was the compound S.

EXAMPLE 5

From the compound S obtained in Example 4 was eliminated benzoyl group as the protective group, to synthetically prepare [6]-shogaol (of the following formula (13)).

[6-]-shogaol;

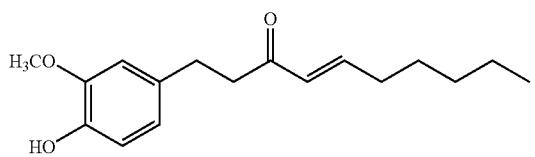

(13)

The compound S of 330 mg (0.867 mmol) was dissolved in 6 ml of N,N-dimethylformamide, to which 0.9 ml of aqueous 1N sodium hydroxide solution was added for agitation at ambient temperature for 2 hours. After 2 ml of 0.5N hydrochloric acid was added, then., extraction with 50 ml of distilled water and with 30 ml of a mixture of n-hexane and ethyl acetate (volume ratio=2:1) and 20 ml thereof was done. The combined organic layers were dried over anhydrous magnesium sulfate and concentrated. The residue was purified by silica gel thin layer chromatography, to obtain a compound of 198 mg in colorless liquid (yield of 83%).

The chemical shift values of the product on $^1$H-NMR spectrum as measured in methanol-d1 agreed with the values described in the reference [C. C. Chem., et al., J. Chromatogr. 360 (1986) 175]. It was thus verified that the compound was [6]-shogaol.

EXAMPLE 6

A test of [6]-shogaol obtained in Example 5 about the inhibition of the activity of mushroom-derived tyrosinase was done, using L-dopa as a substrate.

Consequently, it was shown that [6]-shogaol had an inhibitory activity at the same level as that of arbutin (manufactured by Tokyo Kasei Kogyo Co., Ltd.).

INDUSTRIAL APPLICABILITY

By the production method of the invention, shogaols useful in the fields of for example foods, flavor, pharmaceutical products, qui-pharmaceutical products and cosmetics can be readily produced.

The invention claimed is:

1. A compound represented by the following general formula (1):

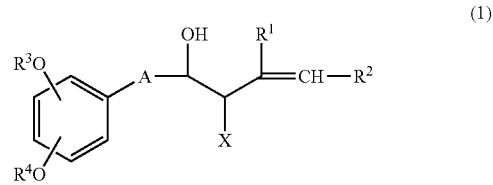

(1)

in the general formula (1), $R^1$ represents hydrogen atom or methyl group; $R^2$ represents optionally branched alkyl group with one to 18 carbon atoms; $R^3$ and $R^4$ each independently represents hydrogen atom, a lower alkyl group or a protective group for phenolic hydroxyl group; A represents an alkylene group with one to 4 carbon atoms; and X represents benzenesulfonyl group or toluenesulfonyl group.

2. A process for producing a shogaol represented by the following general formula (2) from a compound represented by the following general formula (1):

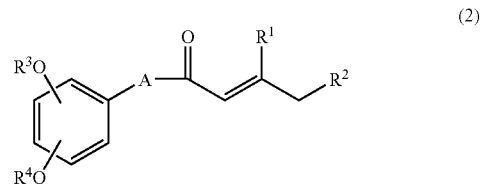

(2)

in the general formula (2), $R^1$ represents hydrogen atom or methyl group; $R^2$ represents optionally branched alkyl group with one to 18 carbon atoms; $R^3$ and $R^4$ each independently represents hydrogen atom, a lower alkyl group or a protective group for phenolic hydroxyl group; and A represents an alkylene group with one to 4 carbon atoms;

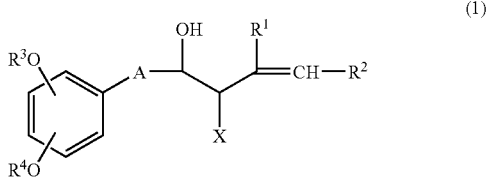

in the general formula (1), $R^1$ represents hydrogen atom or methyl group; $R^2$ represents optionally branched alkyl group with one to 18 carbon atoms; $R^3$ and $R^4$ each independently represents hydrogen atom, a lower alkyl group or a protective group for phenolic hydroxyl group; A represents an alkylene group with one to 4 carbon atoms; and X represents benzenesulfonyl group or toluenesulfonyl group, comprising reacting said compound represented by the general formula (1) with a metal catalyst to form a π-allyl complex and decomposing the π-allyl complex to form said shogaol.

3. The process of claim 2, wherein said π-allyl complex reacts with a basic compound to decompose said π-allyl complex.

4. The process of claim 3, wherein said basic compound is present during the reaction to form said π-allyl complex.

5. The process of claim 2, wherein said metal catalyst is at least one metal catalyst selected from the group consisting of a palladium complex compound.

6. The process of claim 2, wherein the amount of said metal catalyst is 0.0001 to 1 mol per one mol of the compound of general formula (1).

7. The process of claim 2, wherein the amount of said metal catalyst is 0.0005 to 0.05 mol per one mol of the compound of general formula (1).

8. The process of claim 3, wherein said basic compound is a tertiary amine.

9. The process of claim 8, wherein said tertiary amine is at least one tertiary amine selected from the group consisting of triethylamine, diisopropylethylamine, N-methylimidazole, and pyridine.

10. The process of claim 3, wherein the amount of said basic compound is within the range of 1.0 mol to 10 mol per one mole of the compound of general formula (1).

11. The process of claim 3, wherein said basic compound is also a solvent.

12. The process of claim 2, wherein said reacting is carried out in the presence of a solvent.

13. The process of claim 12, wherein said solvent is at least one solvent from the group consisting of tetrahydrofuran, 1,4-dioxane, diethyl ether, 1,2-dimethoxyethane, acetonitrile, chloroform, dichloromethane, 1,2-dichloroethane, hexametbylphosphoric criamide, N,N-dimethylprapylene urea, methanol, ethanol, isopropyl alcohol, ethylene glycol, and glycerin.

14. The process of claim 12, wherein said solvent is a mixture of 1,2-dichloroethane, isopropyl alcohol and glycerin.

15. The process of claim 2, wherein said reacting is conducted within a temperature range of 50° C. to 120° C.

16. The process of claim 2, further comprising purification by at least one method selected from the methods consisting of solvent extraction and column chromatography.

17. The process of claim 2, wherein at least one $R^3$ and $R^4$ in the general formula (2) are protective groups of phenolic hydroxyl group.

18. The process of claim 2, wherein in general formula (2) $R^1$ and $R^3$ are each a hydrogen atom, $R^2$ is a butyl group, $R^4$ is a methyl group, and A is an ethylene group.

19. The compound of claim 1, wherein $R^1$ and $R^3$ are each a hydrogen atom, $R^2$ is a butyl group, $R^4$ is a methyl group, and A is an ethylene group.

* * * * *